(12) United States Patent
Willimann et al.

(10) Patent No.: US 7,674,860 B2
(45) Date of Patent: Mar. 9, 2010

(54) REDISPERSIBLE POWDER AND ITS AQUEOUS DISPERSION, PREPARATION, PROCESS AND USE

(75) Inventors: Hongli Willimann, Baar (CH); Robert Koelliker, Oberkirch (CH)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 11/955,342

(22) Filed: Dec. 12, 2007

(65) Prior Publication Data

US 2008/0090980 A1    Apr. 17, 2008

Related U.S. Application Data

(60) Division of application No. 11/435,044, filed on May 16, 2006, now abandoned, which is a continuation of application No. 09/744,082, filed as application No. PCT/EP99/05200 on Jul. 21, 1999, now abandoned.

(30) Foreign Application Priority Data

Jul. 22, 1998   (DE)   ................ 198 33 062

(51) Int. Cl.
   *C08F 2/22*      (2006.01)
   *C08F 291/00*    (2006.01)
(52) U.S. Cl. .................. 525/242; 524/458; 526/201
(58) Field of Classification Search ................ 526/201; 524/458; 525/242
   See application file for complete search history.

(56) References Cited

U.S. PATENT DOCUMENTS

| | | | |
|---|---|---|---|
| 4,235,982 A | 11/1980 | Maslanka et al. | |
| 4,483,959 A | 11/1984 | Maslanka et al. | |
| 4,871,594 A | 10/1989 | Bister et al. | |
| 5,171,764 A | 12/1992 | Katayama et al. | |
| 5,288,782 A | 2/1994 | Nakajima et al. | |
| 5,403,894 A * | 4/1995 | Tsai et al. | 525/285 |
| 5,688,870 A * | 11/1997 | Wilkinson et al. | 525/244 |
| 5,925,447 A | 7/1999 | Gust et al. | |
| 6,011,103 A | 1/2000 | Inoue | |
| 6,224,981 B1 | 5/2001 | Richard et al. | |

FOREIGN PATENT DOCUMENTS

| | | |
|---|---|---|
| EP | 286 008 | 10/1988 |
| EP | 441 037 | 8/1991 |
| EP | 0 696 602 | 4/1995 |
| EP | 0 522 791 | 3/1996 |
| EP | 0 426 391 | 9/1996 |
| EP | 0 758 658 | 2/1997 |
| EP | 630 909 | 10/1998 |
| JP | 46-22922 | 6/1971 |
| JP | 55-104 955 | 8/1980 |
| WO | WO 96/41825 | 12/1996 |

OTHER PUBLICATIONS

P.A. Lovell et. al. "Emulsion Polymerization and Emulsion Polymers", 1997, pp. 293-326.
T.G. FoxBull, Am. Phy. Soc. (Ser II) 1, 123 (1956).
Ullmann's Enzyklopadie der Technisehem Chemie, vol. 19, 4th edition, Verlag Chemie, Weinheim. 1980, pp. 17-18.
Ullmann's Encyclopedia of Industrial Chemistry, VCH, Weinheim, vol.A21 (1992), p. 169.

* cited by examiner

Primary Examiner—Kelechi C Egwim
(74) Attorney, Agent, or Firm—Kenyon & Kenyon LLP

(57) ABSTRACT

The invention relates to a redispersible powder obtainable by (co)polymerization, using a polymer with cationic functionality in an aqueous medium, optionally accompanied by the use of conventional additives, the polymer with cationic functionality being obtained by (co)polymerization in an aqueous medium of olefinically unsaturated (co)monomers, wherein at least one (co)monomer has a cationic functionality, further (co)monomers are added and polymerization takes place in the presence of suitable initiators, and by drying the aqueous dispersion obtained, the (co)polymerizate having one or more reactive groups. According to another embodiment, the polymer with cationic functionality is formed in situ in the presence of a seed. According to another embodiment, the process is controlled in such a way that a (co)polymerizate particle with heterogeneous morphology is formed. The invention also relates to the aqueous dispersions, a process for the preparation of the redispersible powder and the use thereof.

15 Claims, No Drawings

REDISPERSIBLE POWDER AND ITS AQUEOUS DISPERSION, PREPARATION, PROCESS AND USE

CROSS REFERENCE TO RELATED APPLICATIONS

The present application is a divisional application of U.S. application Ser. No. 11/435,044, filed 16 May 2006, which is a continuation of U.S. application Ser. No. 09/744,082, filed Mar. 16, 2001, abandoned, which is a § 371 national stage filing of PCT/EP99/05200, filed 21 Jul. 1999, abandoned, which claims the benefit of German application 198 33 062.6, filed 22 Jul. 1998, abandoned.

BACKGROUND OF THE INVENTION

1. Technical Field

The present invention relates to a redispersible powder, its aqueous dispersion, a process for the preparation of the redispersible powder and the use of the powder and dispersion.

2. Background Information

The stabilization of aqueous polymer dispersions (latices) is known from the prior art. As opposed to polymer solutions, aqueous polymer dispersions are not thermodynamically stable systems. Therefore, generally dispersing agents having an interfacial stabilizing action are added to the dispersions. Normally they are water-soluble compounds either in the form of protective colloids or emulsifiers. Protective colloids have a stabilizing action due to a steric or electrostatic shielding action, whereas emulsifiers stabilize the polymer dispersion due to their amphiphilic structure. These stabilizers, which can also be used in emulsion polymerization, are conventional surfactants, i.e., water-soluble polymers, such as polyvinyl alcohol or polyvinyl pyrrolidone.

Besides stabilized, aqueous polymer dispersions, the powders obtainable as a result of drying these dispersions are of great significance. Due to their easy handling, easier, space-saving transportation, easier dosability and less expensive storage, redispersible powders are advantageous. Due to the fact that the dispersing medium "water" is everywhere readily available, the powder form is also desirable in this connection. The drying processes for obtaining the redispersible powder are, e.g., performed by means of freeze or spray drying using protective colloids, such as polyvinyl alcohol. A particularly advantageous process for drying aqueous dispersions is spray drying and then larger powder quantities can be produced. In this process, the aqueous dispersion is sprayed in a hot air flow and dewatered and preferably the drying air and sprayed, aqueous dispersion pass in parallel flow form through the drier and, if necessary, known drying aids can be concomitantly used.

A problem when using surfactants or protective colloids is coalescence, i.e. the undesired flowing together of the latex particles in the emulsion, so that it is no longer possible to obtain redispersible powders. This agglomeration to larger polymer secondary particles (coagulate), for a given polymerizate content of the aqueous dispersion, becomes all the more critical the more finely divided the dispersed particles, because the interface grows in super-proportional manner with decreasing particle diameter.

A corresponding powder should admittedly be completely reversibly dispersible, but on adding water generally completely satisfactory results do not occur. This is linked with the fact that on drying the highly dispersed particles in the dispersion necessarily approach one another until in the case of contact of the surfaces of the particles irreversible changes occur, such as the aforementioned coalescence or also an aggregation of the particles. As a result the surface characteristics of the disperse phase are so modified that on adding water, the affinity of the particles to one another is greater than that to water, so that there is no longer any real redispersion.

The aforementioned emulsifiers or protective colloids, such as, e.g., polyvinyl alcohol, can also give rise to a reduction in the reactivity of the redispersed polymer particles. In other words, the redispersible powder, following redispersion, partly or entirely loses its reactivity and consequently the characteristics associated therewith, so that the further reaction of the copolymerized, functional monomers, after dispersion, is greatly impaired or does not occur. One possibility for obtaining stabilized dispersions from water-insoluble latex is known from EP 441 037 A1. The latter describes anionically stabilized dispersions from latex and a quaternary, cationic polymer, preferably a polyamide epichlorohydrin resin, the two components being separately prepared and stored as soluble polymers. Both components are sprayed together onto the application surface, so as to form a dry coating which cannot be washed out, the cationic polymer serving as a flocculant. Therefore the cationic polymers do not contribute to the stabilization of the dispersion and instead destroy the latter, accompanied by the precipitation of the latex polymers (so-called demulsification) and the formation of a coating. No mention is made of redispersible powders.

EP 286 008 B1 describes the use of aqueous, cationic plastic dispersions for impregnating and priming absorbent substrates. The cationic dispersion polymerizates contain 80 to 99 wt. % ethylenically unsaturated monomers from the group vinyl esters, methacrylic esters, acrylic esters, vinyl aromatics, vinyl chloride, ethylene, acrylonitrile. diesters of maleic acid and/or fumaric acid, vinyl pyrrolidine, 1 to 20 wt. % ethylenically unsaturated, cationic, water-soluble monomers, 0 to 19 wt. % ethylenically unsaturated, hydrophilic monomers with one or more functional groups from the series COOH, —$NR^1R^2$, —$CONR^1R^2$, in which $R^1$ and $R^2$ stand for H or —$CH_2OR$ with R=H or ($C_1$ to $C_8$) alkyl and up to 19 wt. % ethylenically unsaturated monomers with one or more OH groups. The monomers are chosen in such a way that the minimum cationic activity of the dispersion is 20 to 200 μmole/g solids, measured at pH 7, and 60 to 99% of the cationic charge is on the surface of the particles and the dispersions have a minimum film formation temperature (MFT) between 0 and 40° C. The polymerizate particles of the dispersions have an average diameter of 0.02 to 0.2 μm. The cationic dispersions are used in impregnating and priming brickwork, concrete, plaster surfaces, ground plaster, gypsum surfaces or bricks. However, dispersible powders are not described.

JP 55-104 955 A describes an aqueous dispersion of a cationic, ethylenically unsaturated polymer having a glass transition temperature Tg<50° C. and containing a cationic, water-soluble or water-dispersible, ethylenically unsaturated oligomer and/or polymer and/or cationizable, ethylenically unsaturated monomers in the aqueous phase. The polymers serve as additives for improving the characteristics of cement products. As a result the water resistance, water tightness, strength, adhesion, chemical stability and durability of a cement product, such as mortar are improved. The emulsion polymerization of said monomers is either brought about by radical polymerization of alpha or beta-ethylenically unsaturated monomers in the presence of cationic, water-soluble and/or water-dispersible oligomers and/or polymers or by radical polymerization of alpha or beta-ethylenically unsaturated monomers, which are in part replaced by cationic, ethylenically unsaturated monomers, such as dimethylaminoethyl methacrylate esters of maleic acid, fumaric acid, itaconic acid, etc.

A disadvantage of this teaching is on the one hand the very restricted range of polymers which can be used, together with the very restricted field of use for cement formulations.

The polymers produced must have a glass transition temperature Tg<50° C. in order to give mortars the desired characteristics. Moreover, the cationic acrylic resin according to this Japanese patent serves as a water dispersing agent and is used as an additional additive. Thus, the use of the cationic, water-soluble or water-dispersible oligomer and/or polymer serves to prevent the coagulation of the latex in the cement. JP 55-104 955 A also fails to describe a redispersible powder, which is also not provided. For the above reasons it is much more difficult, in addition to a stable dispersion, to provide a redispersible powder obtainable therefrom.

JP 46-22922 describes a process for the preparation of cationic vinyl polymer emulsions, the monomer being a diene and/or vinyl compound, which is polymerized in the presence of a water-soluble, thermosetting, cationic resin. The resin is prepared by reacting water-soluble, unmodified or modified homopolyamide resins, which substantially only contain secondary amino groups, with epihalohydrins in water and use can also be made of a nonionic emulsifier. Emulsions prepared in this way are used for improving the strength, water resistance, thermal stability and adhesion of emulsion polymer films in paper manufacture and processing or also in cement formulations. JP 46-22922 does not describe redispersible powders. The very restricted range of starting materials used is disadvantageous here.

SUMMARY OF THE INVENTION

The problem of the invention is to provide redispersible powders from stabilized, aqueous dispersions, whilst maintaining the advantageous characteristics of the powders following redispersion in an aqueous medium, or even improving these characteristics. Further, additional functional groups are to be present in the redispersible powder which are not deactivated after redispersion and the final applications, such as e.g. in plastics-containing, cement-bound systems, lead to improved use products as a result of desirable consecutive reactions. In addition, the choice of starting materials is to be made more flexible. The use of stabilizing additives in the form of emulsifiers and protective colloids, as well as drying or spraying aids is to be substantially obviated.

According to the invention, the above problem is solved by a redispersible powder obtainable by (co)polymerization, using a polymer with cationic functionality in an aqueous medium, optionally accompanied by the use of conventional additives, the polymer with cationic functionality being obtained by (co)polymerization in an aqueous medium of olefinically unsaturated (co)monomers, wherein at least one (co)monomer has a cationic functionality, further (co)monomers are added and polymerization takes place in the presence of suitable initiators, and by drying the aqueous dispersion obtained, the (co)polymerizate having one or more reactive groups.

DESCRIPTION OF THE INVENTION

Thus, at the start of emulsion polymerization a type of protective colloid in the form of a polymer with cationic functionality is made available and which serves as a latex stabilizer. The polymer can be provided beforehand or obtained by homo or (co)polymerization of functional monomers, which optionally contain reactive groups, with one or more cationic, olefinically unsaturated monomers in situ. Surprisingly, the polymers with cationic functionality have for the inventively preparable, redispersible powders an action corresponding to an emulsifier or a protective colloid and even during emulsion polymerization lead to a stabilization of the dispersed, copolymerized particles. Through a type of 'polymerizing in' of the polymer with cationic functionality, a dispersion-stable latex particle is produced and additionally specific functionalities can be applied to the latex surface, particularly for a desired reaction after redispersion has taken place.

It is of great significance for the solution of the set problem, that at least one or several reactive groups are present in the (co)polymerizate prepared. It is not important whether the reactive group or groups are present in the polymer with cationic functionality, in the in situ monomers for producing this polymer and/or in the (co)monomers. The reactive group or groups are preferably a hydroxyl, carboxyl, carboxylate, amino, ammonium, amide, silane, epoxide, carbonyl, formamide, acetamide, succinimide and/or epihalohydrin group. In this way redispersible powders are obtainable, which can be prepared from dispersions with the same reactive groups (e.g., a type of dispersion). In addition, the reactive groups introduced can also comprise different groups (e.g., dispersion with several reactive centers).

Following redispersion of the powder, the introduced reactive groups can be reacted with conventional chemical reactions, e.g. by modifying the pH-value. This can in particular be used for crosslinking the dispersed particles for film formation. Reference is also made to a pH-controlled (self) crosslinking of the dispersions. It is also possible according to the invention, by a corresponding modification of the pH-value in the aqueous medium, to convert the groups present in the (co)polymerizate, which are initially in deactivated form, into reactive groups. The modification of the pH-value can be achieved either through the addition of a corresponding solid, e.g., a solid acid, such as citric acid or oxalic acid, or a solid base, such as calcium hydroxide, sodium hydroxide or cement, to the powder, or said pH-modification can be obtained by corresponding components being present in the matrix, to which the powder is added and mixed.

Through the introduction of reactive groups, it is possible in planned manner to vary the characteristics of the desired end products. For example, the presence of epichlorohydrin groups improves the processability of mortars with regards to wet adhesion. For example, the epichlorohydrin groups can be transformed by corresponding pH-value modification into the corresponding epoxides, which are consequently brought into a reactive form and can subsequently crosslink to polymers, e.g. with amino groups. This plays a part e.g. with single-component epoxy/hardener powders and during redispersion a pH-controlled crosslinking can take place. As a result of their good cross-linking in the acid range, N-methylol acrylamide groups bring about improved processing characteristics for (wood) adhesives. Carboxyl groups improve the processability or setting behavior of cement products. For example, acrylic acid groups are deprotonated on increasing the pH and can form complexes with $Ca^{2+}$ ions and crosslink. In the deprotonated form, they can react with an epoxide. Silanes e.g. hydrolyze with an increased/decreased pH-value to reactive silanol, such as Coatosil® 1706 and have an excellent setting behavior (adhesion) following crosslinking with a substrate (e.g., mortar, wood, glass).

According to the invention, the expression "polymer with cationic functionality" is not specifically restricted, provided that it is obtained by (co)polymerization in aqueous medium of olefinically unsaturated (co)monomers and in the molecule is present at least one cationic function and optionally at least one reactive group. The term "polymer" covers homopolymers, copolymers, block polymers or graft copolymers, as well as oligomers. It is obvious to the expert that numerous (co)polymerizable starting monomers can fulfill the requirements for producing such polymers.

The polymer results from an olefinically unsaturated monomer with cationic functionality, which is e.g. an amino acrylate or methacrylate ester, a vinyl pyridine, an alkylamino group-containing vinyl ether or an alkylamino group-containing acrylamide/methacrylamide. Preferably the cationic functionality is attributed to a quaternary ammonium group. Particularly preferred monomers according to the invention for the preparation of the polymer with cationic functionality are e.g. N,N-[(3-chloro-2-hydroxypropyl)-3-dimethyl ammonium propyl]-methacrylamide chloride (DMAPMA-epi), N-[3-dimethylamino)-propyl]-methacrylamide hydrochloride (DMAPMA-HCl), N-[3-(trimethyl ammonium)propyl]-methacrylamide chloride (MAPTAC), 2-hydroxy-3-methacryloxy-propyl-trimethyl ammonium chloride, dimethyl diallyl ammonium chloride, aziridine ethyl methacrylate, morpholino ethyl methacrylate, trimethyl ammonium ethyl methacrylate chloride, dimethyl aminopropyl-methacrylate, 1,2,2,6,6-penta-methyl piperidinyl methacrylate, aminopropyl vinyl ether, diethyl aminopropyl ether and t-butyl aminoethyl methacrylate or the like.

Thus, according to the invention, the polymer with cationic functionality can either be prepared in a preceding step by homo or (co)polymerization of monomers with cationic functionality or with further (co)monomers and immediately, without being isolated, further processed (in situ further processing), or the polymer with cationic functionality, independently of the inventive process, can initially be separately prepared and isolated prior to the further processing according to the invention. It is obviously possible to use any commercially available polymer with cationic functionality, which fulfils the indicated requirements. Preferably, the polymer with cationic functionality or the in situ produced polymer represents about 0.5 to 50, particularly about 1 to 30 wt. % of the total monomer weight.

With regards to the choice of the (co)monomers, which are polymerized in the presence of the cationic polymer, no particular restriction is made by the present invention. It is possible to use all known (co)polymerizable monomers, which optionally have at least one reactive group. In exemplified manner reference is made to (meth)acrylic acids, vinyl sulfonic acids, vinyl toluene sulfonic acids, unsaturated, dibasic acids, their hemi-esters and salts, alpha-beta-unsaturated amides, vinyl esters, vinyl-substituted, aromatic compounds, heterocyclic compounds with vinyl groups, vinylidene halides, alpha-olefins, diallyl phthalates, divinyl benzenes, alkylacrylates, trimethylol propane trimethyl acrylates, alpha,-beta-ethylenically unsaturated monomers, such as acrylate esters, methacrylate esters, carboxylate esters with methanol, ethanol, propanol, butanol, styrene and styrene derivatives, such as alpha-methyl styrene, o-, m- and p-methyl styrene, o-, m- and p-ethyl styrene, o,p-dimethyl styrene, o,p-diethyl styrene, isopropyl styrene, o-methyl-p-isopropyl styrene, p-chloro styrene, p-bromo styrene, o,p-dichloro styrene, o,p-dibromo styrene, alcohols, polyols, glycidyl alcohols, glycols, polycarboxylic acids and silanes.

Preferably, apart from cationic monomers, monomers are used copolymerized, whose additional, protonated, reactive group or groups, accompanied by a corresponding rise in the pH-value are deprotonated. Such groups are known to the expert and are, e.g., amino groups. According to the invention, it is also possible to use (co)monomers, which additionally have an anionic functionality. This leads to amphoteric systems, which are stable as such and do not coagulate. These surprising characteristics are not described in this form in the prior art.

The reactive monomers preferably represent about 2 to 100, particularly 10 to 100 wt. % of the polymer with cationic functionality. Preferably, in the (co)polymerizate obtained, for about 1 part by weight monomer with cationic functionality of the polymer (with cationic functionality) there are about 2 to 250; particularly, about 4 to 100 parts by weight of other (co)monomers. According to the invention, the (co)polymerizate produced contains about 0.001 to 50, particularly about 0.1 to 35 mole % monomer units with cationic functionality.

According to an alternative embodiment, the polymer with cationic functionality can be formed in situ in the presence of a seed, i.e., there is the preceding additional process step of seed polymerization. In seed polymerization, which is particularly suitable for producing monodisperse particles, latex with a uniform particle size is provided beforehand. Into said seed latex are dosed the monomers to be polymerized in a monomer feed procedure. Polymerization is performed in such a way that the previously provided latex particles increase in volume, but not quantitatively, whilst maintaining the monodispersity of the system. The number of particles is proportional to the fraction provided beforehand and narrow particle size distributions are obtained. For the formation of the seed, according to the invention use is made of about 0.1 to 25, particularly about 0.5 to 20 wt % of the (co)monomer based on the finished (co)polymerizate.

The powders according to the invention, whose dispersions are prepared using a preceding seed polymerization, have an extremely homogeneous particle size, i.e. the particles are monodisperse. In this context, "monodisperse" means that the average particle diameter preferably varies by about ±10%. Such homogeneous particle sizes are difficult to obtain with the known prior art processes or can only be prepared with considerable process engineering expenditure and low yields. Thus, in the present invention, the particle size can be set in a planned manner. The latex particles formed in the redispersible powder preferably have an average diameter of about 30 to 1000 nm, particularly about 50 to 600 nm.

In another variant, the polymers and/or (co)monomers can be so chosen and the process so controlled, that a (co)polymerizate particle with heterogeneous morphology is formed. In this context "heterogeneous morphology" means that two or more different glass transition temperatures Tg need not necessarily be present. In other words, the (co)polymerizate particles have areas with different compositions. According to the invention, it can, e.g., be inverse core-shell morphology with a substantially hydrophilic, inner phase (core) and a substantially hydrophobic, outer phase (shell). According to the invention, a so-called raspberry-like structure can be produced. It is obviously also possible to obtain mixed forms with heterogeneous morphology. Preferably the emulsion polymerization is performed in such a way that the proportion of polymer with cationic functionality in the outer phase is greater than in the inner phase. The parameters and conditions variable in this connection are known to the expert and reference is made to "Emulsion Polymerization and Emulsion Polymers", P. A. Lovell and M. S. El-Aasser, 1997, pp. 293-326.

For example, the glass transition temperature Tg of the inner and outer phases can in each case be modified, so as to permit an adaptation to the intended use. As is known, by the choice and quantity of the monomers used, the glass transition temperature can be controlled. The criteria for adjusting the glass transition temperature to be used in the process according to the invention are known to the expert. The weight proportions of the possible (co)monomers are chosen in such a way that the glass transition temperature Tg (midpoint temperature according to ASTM D3418-82) of film formation of the redispersible particles prepared gives the desired, modifying action, Tg generally being in a range of −70 to 110° C. In general, the glass transition temperature can be determined by measurement, e.g. by DSC methods or by theoretical calculation. According to the invention, the glass transition temperature of the (co)polymers is calculated according to the Fox trial and error method (T. G. Fox, Bull. Am. Phy. Soc. (Ser II) 1,123 (1956) and Ullmann's Enzyklopädie der Technischen Chemie, vol. 19, 4th edition, Verlag Chemie, Weinheim, 1980, pp 17/18). Thus, for the glass transition temperature is obtained:

$$\frac{1}{Tg} = \frac{W_A}{Tg_A} + \frac{W_B}{Tg_B} + \ldots \frac{W_n}{Tg_n}$$

in which $$W_A + W_B + W_C \ldots = 1$$

and $W_A$, $W_B$, ... stand for the mass fractions of the monomers a, b ... and $Tg_A$, $Tg_B$ ... the glass transition temperatures of the corresponding (co)polymers. The glass transition temperatures of certain homopolymerizates of the aforementioned monomers are known and are listed, e.g., in ULLMANN'S ENCYCLOPEDIA OF INDUSTRIAL CHEMISTRY, VCH, Weinheim, Vol. A21 (1992), p. 169.

According to a preferred embodiment, the Tg-value of the outer phase is as high as possible and simultaneously the Tg-value of the inner phase is as low as possible. Preferably, e.g., the glass transition temperature Tg of the inner phase is below 50° C. and the glass transition temperature Tg of the outer phase above 50° C. If very rapid film formation is desired, then preferably the inner phase has a very low Tg-value, preferably below 50° C., so that latex particle coalescence occurs. This is advantageous if an elastifying action of the (co)polymerizate particles is desired. In certain cases it can be advantageous to choose a glass transition temperature Tg below 0° C. The Tg-range of 0 to 25° C. is e.g. suitable for modifying repair mortars.

If a rapid film formation does not have to take place at ambient temperature, the glass transition temperature Tg is above 50° C. In corresponding applications this can be of importance, because as a result the stability of the redispersible powders is increased and higher mechanical characteristics are obtained in the final application. In certain cases it can be advantageous to choose a film-forming temperature of the (co)polymerizate above 10° C.

Advantageously powders composed of latex particles generally have a much better storage stability and water resistance than products without heterogeneous morphology. The functional groups present in the inner phase are protected by the outer phase. Preferably, the inner phase is completely surrounded by the outer phase. Through the addition of a base, the polymer in the inner phase can be dissolved out by at least partial neutralization and therefore completely diffuses out of the outer phase. Suitable bases are so-called swelling agents. for which the hydrophobic polymer of the outer phase is permeable, in order to bring about a swelling of the polymers. Suitable swelling agents include bases, such as ammonia, ammonium hydroxide and volatile, lower aliphatic amines, such as morpholine, trimethyl amine and triethyl amine. It is also possible to use potassium hydroxide, lithium hydroxide, zinc ammonium complexes, copper ammonium complexes, silver ammonium complexes, strontium hydroxide, barium hydroxide, etc.

Thus, the outer phase fulfils the function of a protective shield, which both in aqueous dispersion and in powder form protects the reactive groups of the polymers of the outer phase, e.g. carboxyl groups, against immediate reaction. As a result, in planned manner there can be a delayed release of the polymer of the inner phase in controlled portions through the addition of one of the aforementioned bases. As a result of the delayed release, it is possible to prevent an immediate sequestration, e.g. of the carboxyl group with metal ions in the cement, or other undesired blocking via electrostatic interaction of the reactive groups. The prevention of a direct reaction of the reactants is advantageous if a longer processing or working time is necessary and an excessively rapid complete reaction of the components in the form of setting, curing, etc. is to be avoided. This effect according to the invention is not impaired by very high concentrations of the reactive groups of the core polymer, which can be attributed to the planned, homogeneous distribution of the reactive groups of the core polymer.

In addition to the heterogeneous morphology, once again a seed polymerization can be performed during the production of the cationic polymer, as was described hereinbefore, The (co)polymerizate particles prepared by means of the preceding seed polymerization have, according to this variant, not only the advantages associated with heterogeneous morphology, but additionally a substantially homogeneous particle size distribution and are consequently so-called monodisperse particles.

According to a preferred embodiment a further powder can be admixed to the redispersible powder according to the invention which results in an optimization of the properties. Thus, powder 1 with one kind of latex particles is mixed with a further powder 2 of other latex particles. In a preferred manner, the weight ratio of powder 1 to powder 2 is in a range of about 5:95 to 95:5, preferably about 10:90 to 90:10, particularly about 20:80 to 80:20. The powder 2 can comprise homopolymers or copolymers selected from the following monomers: vinyl acetate, ethylene. vinyl versatate, acrylate, methacrylate, styrene and/or butadiene. This listing is only exemplary; there is no limitation. As a matter of course, an expert of this technical field knows further monomers which can be used herein.

The invention also relates to aqueous dispersions of the above-described redispersible powders.

It is preferred that the obtained aqueous dispersion (dispersion 1) of one kind of latex particle can be admixed with a further aqueous dispersion (dispersion 2) of other latex particles. The weight ratio of dispersion 1 to dispersion 2 is in the range mentioned for the above powder. By adding dispersion 2 in form of an aqueous dispersion of homopolymers or copolymers with the monomers vinyl acetate, ethylene, vinyl versatate, acrylate, methacrylate, styrene and/or butadiene the properties of the dispersion can be optimized accordingly and adapted to the intended use. The above monomers are only examples and the listing is not limited.

The invention also relates to a process for the preparation of a redispersible powder, comprising (co)polymerization using a polymer with cationic functionality in an aqueous medium, accompanied optionally by the addition of conventional additives. The polymer with cationic functionality is obtained by (co)polymerization in the aqueous medium of olefinically unsaturated (co)monomers, in which at least one (co)monomer has a cationic functionality, further (co)monomers are added and polymerization takes place in the presence of suitable initiators, and by drying the aqueous dispersion obtained, the (co)polymerizate having one or more reactive groups. In an alternative, the polymer with cationic functionality can also be formed in situ in the presence of a seed. The polymers and/or (co)monomers can also be so chosen and the process so controlled, that a (co)polymerizate particle with heterogeneous morphology is formed. To avoid unnecessary repetition for details, reference should be made to the above statements.

The emulsion polymerization for preparing the redispersible powder can be performed continuously, semi-continuously or as a batch process. This is dependent on whether the polymer with cationic functionality is prepared separately or processed further directly after in situ preparation. For example, following the production of the cationic polymer, the process can be performed batchwise. It is also clear to the expert that for performing the process, due account must be taken of the fundamental rules of emulsion polymerization. Thus, e.g. radical initiators are used for performing the polymerization. With regards to the choice of initiators, no relevant restrictions exist in the present invention. The radical initiators used within the scope of the invention are either water-soluble or water-insoluble, i.e. they are then monomer-soluble. Suitable, water-soluble initiators are sodium, potassium and ammonium peroxodisulphate, hydrogen peroxide and water-soluble azo compounds, e.g., 2,2'-azobis(2-amidinopropane dihydrochloride), 2,2'-azobis[2-methyl-N(2-hydroxyethyl)-propionamide] and 2,2'-azobis[2-(2-imidazolinyl)-propane]-dihydrochloride. Suitable monomer-soluble initiators are organic hydroperoxides, such as tertbutyl hydroperoxide, pinane hydroperoxide, p-menthane hydroperoxide, cumene hydroperoxide and diisopropylphenyl hydroperoxide, organic peroxides, such as dibenzoyl peroxide, dilauryl peroxide and diacetyl peroxide, as well as monomer-soluble azo compounds, such as azoisobutyronitrile. Particular preference is given to 2,2'-azobis(2-amidinopropane dihydrochloride) and TBHP (t-butyl hydroperoxide). It is also possible to use mixtures of initiators.

In place of a radical initiator, it is also possible to use an initiator system, which comprises a radical initiator of the aforementioned type and a water-soluble reducing agent. The water-soluble reducing agents act as activators for the initiators. Suitable reducing agents are ascorbic acid, sodium, potassium and ammonium sulfite, bisulfite and metabisulfite, sodium formaldehyde sulfoxylate, tartaric acid, citric acid and glucose. They can be used in combination with a heavy metal salt. The reducing agents are generally used in a quantity of 0.01 to 2 wt. %, based on the total monomers added. They are generally dosed in during polymerization. The radical initiator is consequently formed during polymerization, which can e.g. take place by thermal decomposition of the above initiator, but also by the reaction of the initiator with an aqueous reducing agent. The initiators or initiator combination are generally used in a quantity of 0.01 to 2 wt %, based on the total monomers. Particular preference is given to 2,2'-azobis(2-amidinopropane)-dihydrochloride, hydrogen peroxide and t-butyl hydroperoxide combined with a reducing agent, such as e.g. sodium formaldehyde sulfoxylate.

As a function of the use conditions, conventional additives can be concomitantly used. As examples are given thickeners, pigments, flameproofing agents, crosslinkers, fillers, reinforcing agents, film formation aids, antioxidants, fungicides, foam inhibitors, plasticizers, preservatives, wetting agents, rheology modifying aids, vulcanizing agents, resins, adhesive aids, anti-blocking agents, etc., which can be added in standard quantities.

According to the invention, the preparation of the dispersion preferably takes place without surfactants, such as emulsifiers or the like, but optionally a small amount of emulsifier can be used. The emulsifier proportion is appropriately below about 3 and in particular below about 1.5 wt %. Preferably, the emulsifier proportion is below 1.0, in particularly preferred manner below 0.5 and more especially below 0.2 wt %. The emulsifiers or protective colloids conventionally used in emulsion polymerization can be employed.

Polymerization is preferably carried out at between about 50 and 100° C., particularly between about 60 and 90° C. The temperature can e.g. depend on the initiator system used. In certain cases the starting temperature is preferably about 70° C. The heat evolution due to the exothermic reaction during polymerization can be used for setting a reaction temperature at between 80 and 90° C. where cooling may be necessary so as not to exceed the temperature range given. All the heat produced can be dissipated. so as to maintain the starting temperature of about 70° C. throughout the reaction or even to drop below the same. In certain cases it is possible to work in an autoclave, which offers the possibility of polymerizing at above 100° C.

The pH-value of the aqueous dispersing medium during radical, aqueous emulsion polymerization is generally 2 to 10. Following the end of polymerization, the pH-value can be set at 2 to 12.

After obtaining the stabilized, aqueous dispersion, the powder according to the invention can be obtained by removing the water in the conventional manner by drying, particularly by spray or freeze drying. The redispersible powder can be used as a pulverulent finished mixture, which only has to be stirred or mixed with water. As a function of the intended use, it can be redispersed in water in a more or less concentrated form.

With particular advantage the present invention makes it possible to obtain a high solids content in the dispersion prepared, a dispersion with up to about 75% solids content in the aqueous medium being possible. However, appropriately and as a rule an aqueous dispersion is prepared with about 20 to 60, particularly about 30 to 50% solids content.

The redispersible powder and the aqueous dispersions according to the present invention can be used in many different ways. They are suitable for use in composite and coating mortars, cement dyes and adhesives, in plastics-containing, cement-bound systems, particularly in mortars, and plastics-bound, cement-free binders, particularly in cement-free mortars, gypsum mortars, primers, plasters, carpet, wood, powder and floor adhesives, as well as in wallpaper pastes, disperse dyes and glass fiber composite systems. In particular, the (co)polymerizates in the form of redispersible powder prepared as a result of seed polymerization are suitable as filling material for columns in chromatographic separation processes, such as gas chromatography or high pressure liquid chromatography (HPLC), as well as calibrating material for particle size measuring instruments, because, as a result of the preparation process, the particles substantially have the same diameter, i.e., are homogeneous or monodisperse.

According to the invention, the redispersible powder can be used as a carrier for the delayed release of active substances of all types. This can take place by polymerizing the substances into the (co)polymerizate particles or by adding the dispersion, accompanied by stirring and subsequent drying. Such substances are e.g. used in the agricultural sector as fungicides, herbicides, phytohormones, insecticides, nematicides, rodenticides and acaricides. Substances from the food sector are also possible, such as e.g. vitamins, mineral substances, etc. With particular preference, the redispersible powders according to the invention can be used as inert carrier materials for medicaments in the medical sector. This is particularly advantageous as a result of the delayed release, because this permits an easier dosing with a more planned application.

The desired, improved characteristics of the powders obtainable according to the invention are due to the fact that a polymer with cationic functionality in an emulsion polymerization process partly or completely takes over the function of a surfactant or protective colloid, independently of further functionalities in the molecule. It is unimportant whether the polymer with cationic functionality is present in homopolymerized or copolymerized form.

Numerous advantages are associated with the invention. The invention makes it possible to provide reactive, redispersible powders, which following redispersion can undergo further chemical reactions, such as e.g. a crosslinking as a function of the pH-value. As a result extensively crosslinked systems are obtained, which are resistant to water. They can e.g. be used externally without cement, where a high solvent resistance is necessary. The presence of additional reactive groups generally leads to improved characteristics of the products. In a particularly advantageous manner, the reactive functionalities can be brought to the latex surface, i.e., where they evolve their highest reactivities. In addition, the inventive, redispersible powders offer a surprising flexibility compared with the aforementioned prior art teachings with respect to the quantitative and qualitative framework conditions. This is revealed in the characteristics of the particles individually adjustable in planned manner for each application, e.g. through the additional seed polymerization and/or the formation of a heterogeneous morphology. By mixing the redispersible powder of the present invention with a further powder or the aqueous dispersion with a further dispersion, the desired properties can be optimized accordingly. It is particularly advantageous if the dispersed polymerizate particles have a relatively small diameter, which can be produced in planned manner by incorporating seed polymerization. Such monodisperse particles can even meet the high demands of chromatographic separation systems or calibration materials. The inventive, specific latex morphology leads to surprising characteristics of the latex particles. It is possible to encapsulate polymers with reactive groups, so that there is, e.g., a delayed reaction or crosslinking during use. These characteristics are also maintained in the case of high concentrations of reactive groups of the core polymer. The inventive, redispersible powders also offer the possibility of a delayed release and consequently improved dosability as inert carrier materials for numerous active substances, e.g., in the agricultural, food and pharmaceutical sectors. Through the planned selection of the glass transition temperature in the latex particles, there can be an additional adaptation to the desired use. According to the invention, emulsifiers are not necessarily used. This makes it possible to completely exclude the disadvantages associated with such stabilizing additives. It is in fact possible to obviate the use of any further stabilizing agents. The redispersible powders obtained still have very favorable characteristics A particular advantage is that the redispersible powders lead to improved characteristics in the indicated final applications.

The invention is described in detail hereinafter relative to examples, which are not intended to restrict the teaching according to the invention. Within the framework of the inventive disclosure, further examples are apparent to the expert.

EXAMPLES

The following abbreviations are used in the Examples—
MMA Methyl methacrylate
BA Butyl acrylate
MAPTAC N-[3-(trimethyl ammonium)-propyl]-methacrylamide chloride
DMAPMA N-[3-(dimethyl amino)-propyl]-methacrylamide
DMAPMA-epi N,N-[3-(chloro-2-hydroxypropyl)-3-dimethyl ammonium propyl]methacrylamide chloride
AA Acrylic acid
GNA Glycidyl methacrylate
VEOVA®-10 Vinyl ester of Versatic 10® (VEOVA® X is a Shell trademark and stands for vinyl esters of carboxylic acids, which are also known as Versatic® X-acids)
Triton® Rohm & Haas trademark for a range of nonionic surfactants
TBHP-70 t-butyl hydroperoxide, 70% in water
Coatosil® 1706 Vinyl triisopropoxy silanes; OSi Specialties Inc.
NVF N-vinyl formamides
HCl Hydrochloric acid
V-50 2,2'-azobis(2-amidinopropane)-dihydrochloride.

Example 1

To a 2 liter glass reactor, equipped with a stirrer and a thermostat, were successively added 20.7 g of Triton® X-405, 3.6 g dodecyl mercaptan, 0.9 g of acetic acid and 675 g of deionized water. This was followed by scavenging with nitrogen and heating to 80° C., accompanied by stirring. On reaching this temperature, simultaneously 66 g of a 55% aqueous solution of N,N-[(3-chloro-2-hydroxypropyl)-3-dimethyl ammonium propyl]-methacrylamide chloride (hereinafter called DMAPMA-epi) and a mixture of 72.4 g of methyl methacrylate and 72.4 g of butyl acrylate was added over a one hour period. One minute later, 1.3 g of 2,2'-azobis (2-amidinopropane)-dihydrochloride (Wako Chemicals GmbH, hereinafter called V-50) was added in one portion. 15 minutes after the start of the above feeds, 4.9 g of V-50, dissolved in 15 g of water, were dosed in over a three and a half hour period. It was ensured during this time that the temperature was kept at between 79 and 81° C. and 75 minutes after the start of polymerization, a mixture of 272 g of methyl methacrylate and 272 g of butyl acrylate was dosed in over a two and a quarter hour period. When all the feeds had ended, cooling took place to 60° C., followed by dilution with 20 g of water and somewhat later cooling to 30° C., followed by the analysis of the dispersion. The solids represented 49.1%, the viscosity was 1030 mPas (according to Brookfield, spindle 4, 20 rpm) and the pH-value was 4.1.

Example 2

Example 1 was repeated, but 20.7 g of Triton® X-405, 3.6 g of dodecyl mercaptan, 1.0 g of sodium hydrogen carbonate and 670 g of deionized water were added to the reactor. The aqueous monomer solution consisted of 72.4 g of N-[3-(trimethyl ammonium)-propyl]-methacrylamide chloride (50% in water, hereinafter called MAPTAC) and the one-hour monomer feed consisted of 54.3 g of methyl methacrylate, 54.3 g of butyl acrylate and 36.2 g of glycidyl methacrylate. The solids represented 47.0%, the viscosity was 9000 mPas and the pH-value 8.3.

Example 3

Example 2 was repeated, 20.7 g of Triton® X-405, 3.6 g of dodecyl mercaptan 0.9 g of acetic acid and 670 of deionized water being added to the reactor. The one-hour monomer feed consisted of 54.3 g of methyl methacrylate, 54.3 g of butyl acrylate and 36.2 g of N-[3-(dimethyl amino)-propyl]-methacrylamide (hereinafter called DMAPMA). The solids represented 49%, the viscosity was 1940 mPas and the pH-value 8.8.

Example 4

Example 1 was repeated, but 3.6 g of dodecyl mercaptan, 1.1 g of acetic acid and 710 g of deionized water were added to the reactor. The aqueous monomer solution consisted of 67.3 g of DMAPMA-epi and the one-hour monomer feed consisted of 133.4 g of methyl methacrylate and 14.8 of butyl acrylate. The solids represented 47.1%, the viscosity was 400 mPas and the pH-value 1.5.

Example 5

Example 1 was repeated, but 3.6 g of dodecyl mercaptan, 1.0 g of sodium hydrogen carbonate and 680 g of deionized water were added to the reactor. The aqueous monomer solution consisted of 67.3 g of DMAPMA-epi and the one-hour monomer feed 99.9 g of methyl methacrylate, 11.1 g of butyl acrylate and 37.0 g of Coatosil® 1706. The solids represented 47.1%, the viscosity was 1000 mPas and the pH-value 6.5.

Example 6

Example 2 was repeated, but 20.7 g of Triton® X-405, 3.6 g of dodecyl mercaptan, 1.0 g of sodium hydrogen carbonate and 670 g of deionized water were added to the reactor. The aqueous monomer solution consisted of 72.4 g of DMAPMA-epi and 72.4 g of MAPTAC, and the one-hour monomer feed 54.3 g of methyl methacrylate, 54.3 g of butyl acrylate and 36.2 g of glycidyl methacrylate. After 1¾ hours the viscosity rose, so that a further 560 g of water were added to the reactor. The solids represented 30%, the viscosity was 2200 mPas and the pH-value 7.3.

Example 7

Example 1 was repeated, but 3.6 g of dodecyl mercaptan, 0.9 g of acetic acid, 200 g of 1 N hydrochloric acid and 475 g of deionized water were added to the reactor. The aqueous monomer solution consisted of 65.9 g of DMAPMA-epi and the one-hour monomer feed 54.4 g of methyl methacrylate, 54.4 g of butyl acrylate and 36.3 g of DMAPMA. The solids represented 50%, the viscosity was 1380 in mPas and the pH-value 4.8.

Example 8

Example 1 was repeated, but 3.6 g of dodecyl mercaptan, 0.9 g of acetic acid and 645 g of deionized water were added to the reactor. The aqueous monomer solution consisted of 132.1 g of DMAPMA-epi and the one-hour monomer feed of 18.2 g of methyl methacrylate, 18.2 g of butyl acrylate and 72.7 g of acrylic acid. The solids represented 48.4%, the viscosity was 14000 mPas and the pH-value 2.0.

Example 9

To a 2 liter glass reactor, equipped with a stirrer and a thermostat, were successively added 10.0 g of Triton® X-405, 0.8 g of sodium lauryl sulfate, 2.4 g of seed monomer and 450 g of deionized water. This was followed by scavenging with nitrogen and heating to 75° C., accompanied by stirring. On reaching this temperature, simultaneously 35.0 g of a 55% aqueous solution of DMAPMA-epi, together with 60.0 g of deionized water was dosed in over a 30 minute period. 30 minutes after the start of the above feeds, 5.7 g of V-50, dissolved in 60 g of water, were dosed in over a three and a half hour period. It was ensured that throughout the time the temperature was kept at between 74 and 76° C. 30 minutes after the start of polymerization, over a 3 hour period, dosing in took place of a mixture of 252 g of methyl methacrylate, 24 g of acrylic acid, 2.4 g of methacrylic acid and 252 g of butyl acrylate. When all the feeds had ended, cooling took place to 35° C. The solids represented 49.8%, the viscosity was 607 mPas and the pH-value 2.7.

Example 10

The dispersions from examples 4, 5, 8 and 9 were spray dried according to conventional processes. Prior to spraying, dispersions 4, 5 and 8 were mixed with 10 parts of partly hydrolyzed polyvinyl alcohol (degree of hydrolysis 88%, viscosity 4 mPas as a 4% solution) to 90 parts of dispersion. The solids fraction was adjusted with water to 25% and sprayed by means of a two-fluid nozzle. The spraying component was constituted by air precompressed to 4 bar. The droplets formed were dried with air at 110 to 115° C. in parallel flow. In all cases a free-flowing, redispersible powder was obtained.

Comparison Example 1

Example 2 was repeated, but 3.6 g of dodecyl mercaptan, 0.9 g of acetic acid and 670 g of deionized water were added to the reactor. The aqueous monomer solution consisted of 72.4 g of MAPTAC and the one-hour monomer feed of 72.4 g of methyl methacrylate and 72.4 g of butyl acrylate. The solids represented 44%, the viscosity was 520 mPas and the pH-value 4.4.

Example 11

Dispersions of the above examples were poured into Petri dishes and their pH-value, as desired, was adjusted with 1 N caustic soda solution, so that each contained about 5 g of solids. The dispersions were dried at ambient temperature and about 1.5 g of the film obtained was precisely weighed in and added together with 100 ml of acetone to a 250 ml Erlenmeyer flask and left to stand at ambient temperature for 24 hours. The acetone solution was then filtered and duplicate 10 ml of solution were weighed out, dried in the oven and the solids fraction weighed. Using the following formula, the fraction insoluble in acetone was calculated: % insoluble fraction=(1−[weighed out fraction×10])/weighed in film×100%. The results with the dispersions obtained are summarized in the following table.

TABLE 1

| Dispersion from Example No. | pH not adjusted | % insoluble fraction in acetone | |
|---|---|---|---|
| | | pH 10 | pH 13 |
| 1 | 28.0% (pH 4.1) | 64.7% | 73.0% |
| 6 | 68.5% (pH 7.3) | 72.5% | 79.2% |
| 7 | 35.8% (pH 4.8) | 73.6% | ND* |
| Comparison Example 1 | 34.5% (pH 4.4) | ND* | 45.1% |

*ND = Not determined

Example 12

Example 11 was repeated, it being ensured that initially two different dispersions were mixed with one another (the same solids fraction), which contained reactants, which can react with one another. The results with the dispersions obtained are given in Table 2.

TABLE 2

| Dispersions from Examples No. | % insoluble fraction in acetone | | |
|---|---|---|---|
| | pH 3 | pH 7 | pH 10 |
| 1 + 3 | 50.8 | 88.4% | 92.3% |

The results obtained in Tables 1 and 2 are likewise also obtained in the case of dispersions obtained by redispersing the inventive, redispersible powder.

The above examples show that inventive, redispersible powders are obtained. Following the redispersion of this powder, the reactivity of the reactive groups present is surprisingly scarcely lost. This is also shown in the above-determined, insoluble acetone fraction. The higher the percentage of insoluble fraction, the greater the crosslinking obtained by the subsequent reaction of the reactive groups. Thus, the insoluble fraction is a measure for the retained reactivity in the inventive, redispersible powders. This leads to the excellent use and processing characteristics of the inventive, redispersible powders or dispersions.

We claim:

1. Process for preparing film-forming, redispersible polymer powder comprising the steps of:
    polymerizing an aqueous medium of olefinically unsaturated monomers, the olefinically unsaturated monomers having at least one monomer with cationic functionality and at least one monomer with one or more reactive groups or at least one monomer with cationic functionality and one or more reactive groups, thereby obtaining at least one polymer with cationic functionality and one or more reactive groups,
    polymerizing at least one comonomer with at least one initiator in an aqueous medium in the presence of the at least one polymer with cationic functionality and one or more reactive groups to form an aqueous polymer dispersion having particles with heterogeneous morphology and at least one polymer phase with a glass transition temperature below +50° C., and
    drying the aqueous dispersion to obtain the redispersible polymer powder.

2. Process according to claim 1 wherein the olefinically unsaturated monomers further comprise at least one monomer with at least anionic functionality.

3. Process according to claim 1 wherein the at least one polymer with cationic functionality is polymerized in situ in the presence of a seed monomer.

4. Process according to claim 1 wherein the polymer powder comprises latex particles having core-shell morphology.

5. Process according to claim 4 wherein the latex particles have an average diameter of from 30 to 1000 nm.

6. Process according to claim 1 wherein the one or more reactive groups are chosen from hydroxyl, carboxyl, carboxyl ester, amino, ammonium, amide, silane, epoxide, carbonyl, formamide, acetamide, succinimide, epihalohydrin and mixtures thereof.

7. Process according to claim 1 wherein the at least one monomer with cationic functionality comprises 1 to 30 percent by weight of total monomer weight of the redispersible polymer powder.

8. Process according to claim 1 wherein the at least one polymer with cationic functionality is formed from 10 to 100 percent by weight of monomers having at least one reactive group.

9. Process according to claim 1 wherein the at least one monomer with cationic functionality comprises a quaternary ammonium group.

10. Process according to claim 1 further comprising adding the redispersible polymer powders to an aqueous medium forming an aqueous redispersion.

11. Process according to claim 1 wherein the reactive groups are activated by changing the pH of the aqueous dispersion.

12. Process according to claim 1 wherein the reactive groups comprise at least one protonated group able to be deprotonated by changing the pH of the aqueous dispersion.

13. Process according to claim 1 wherein the aqueous dispersion comprises less than 2.5% by weight of emulsifier.

14. Process according to claim 11 wherein the aqueous dispersion is free of emulsifier.

15. Process according to claim 1 wherein drying is by spray or freeze drying.

* * * * *